(12) United States Patent
Ebetsberger et al.

(10) Patent No.: US 10,772,549 B2
(45) Date of Patent: Sep. 15, 2020

(54) HANDLING DEVICE AND METHOD FOR THE PRODUCTION THEREOF

(71) Applicant: Greiner Bio-One GmbH, Kremsmuenster (AT)

(72) Inventors: Franz Ebetsberger, Kremsmuenster (AT); Georg Kofler, Inzersdorf (AT); Florian Oefferlbauer, Nussbach (AT)

(73) Assignee: Greiner Bio-One GmbH, Kremsmuenster (AT)

( * ) Notice: Subject to any disclaimer, the term of this patent is extended or adjusted under 35 U.S.C. 154(b) by 744 days.

(21) Appl. No.: 15/744,972

(22) PCT Filed: Oct. 19, 2015

(86) PCT No.: PCT/AT2015/050259
§ 371 (c)(1),
(2) Date: Feb. 22, 2018

(87) PCT Pub. No.: WO2016/061601
PCT Pub. Date: Apr. 28, 2016

(65) Prior Publication Data
US 2018/0199875 A1 Jul. 19, 2018

(30) Foreign Application Priority Data
Oct. 20, 2014 (AT) .............................. A 50749/2014

(51) Int. Cl.
| | | |
|---|---|---|
| A61B 5/00 | (2006.01) | |
| A61B 5/15 | (2006.01) | |
| A61B 5/154 | (2006.01) | |

(52) U.S. Cl.
CPC .... *A61B 5/150732* (2013.01); *A61B 5/15003* (2013.01); *A61B 5/154* (2013.01);
(Continued)

(58) Field of Classification Search
CPC .......... A61B 5/15003; A61B 5/150343; A61B 5/150351; A61B 5/150374;
(Continued)

(56) References Cited

U.S. PATENT DOCUMENTS

| | | |
|---|---|---|
| 3,585,984 A | 6/1971 | Buchanan et al. |
| 3,734,080 A | 5/1973 | Petterson et al. |

(Continued)

FOREIGN PATENT DOCUMENTS

| | | |
|---|---|---|
| DE | 2 028 662 A | 1/1971 |
| DE | 2903167 A1 | 7/1980 |

(Continued)

OTHER PUBLICATIONS

International Search Report of PCT/AT2015/050259, dated Jan. 5, 2016.
(Continued)

*Primary Examiner* — Max F Hindenburg
(74) *Attorney, Agent, or Firm* — Collard & Roe, P.C.

(57) ABSTRACT

A handling device for medical technology includes a main body part and a front wall which define a receiving space. A cannula protrudes with its proximal cannula end into the receiving space. A hose-like sleeve is held with its distal sleeve end on at least one holding element of the holding device, which holding element is formed or arranged directly on the front wall. The holding element bears externally on the sleeve in a contact area. Moreover, a method produces a handling device of this type.

23 Claims, 6 Drawing Sheets

(52) U.S. Cl.
CPC .. *A61B 5/150389* (2013.01); *A61B 5/150473* (2013.01); *A61B 5/150503* (2013.01); *A61B 5/150572* (2013.01)

(58) Field of Classification Search
CPC ........ A61B 5/150389; A61B 5/150473; A61B 5/150732; A61B 5/15048; A61B 5/150488; A61B 5/150496
See application file for complete search history.

(56) References Cited

U.S. PATENT DOCUMENTS

| | | | |
|---|---|---|---|
| 5,897,508 A | 4/1999 | Konrad | |
| 6,110,160 A | 8/2000 | Faerber | |
| 2004/0215107 A1 | 10/2004 | Sarstedt et al. | |

FOREIGN PATENT DOCUMENTS

| | | |
|---|---|---|
| DE | 2908817 A1 | 9/1980 |
| DE | 203 01 575 U1 | 6/2003 |
| DE | 10 2007 031 799 B3 | 10/2008 |
| EP | 0 803 226 A2 | 10/1997 |
| EP | 1 442 706 A1 | 8/2004 |
| WO | 95/16395 A1 | 6/1995 |
| WO | 2009/006960 A1 | 1/2009 |
| WO | 2015/076221 A1 | 5/2015 |

OTHER PUBLICATIONS

International Preliminary Report on Patentability in PCT/AT2015/050259, dated Apr. 11, 2017.

HANDLING DEVICE AND METHOD FOR THE PRODUCTION THEREOF

CROSS REFERENCE TO RELATED APPLICATIONS

This application is the National Stage of PCT/AT2015/050259 filed on Oct. 19, 2015, which claims priority under 35 U.S.C. § 119 of Austrian Application No. A 50749/2014 filed on Oct. 20, 2014, the disclosure of which is incorporated by reference. The international application under PCT article 21(2) was not published in English.

BACKGROUND OF THE INVENTION

1. Field of the Invention

The invention relates to a handling device, in particular for medical technology, and a method for producing a handling device of this type.

2. Description of the Related Art

EP 0 803 226 A2 discloses a generic blood-taking device with a holder exhibiting a cannula. In the holder, the cannula is held directly on the front wall and has sharpened cutting edges on both sides; the partial section of the cannula that extends into the holder is encased with air by an elastic hose-like valve rubber which is closed at one end. A secure seat of the valve rubber in the holder or adapter is ensured when the section of the holder that immobilizes the valve rubber from the outside is a deformable clamping element. The clamping element can be formed by a surrounding ring or a ring formed of partial segments placed at intervals. The front wall of the holder is formed without discontinuities except for the receiving opening for the double-ended cannula.

DE 29 03 167 A1 describes a holding device with a double-ended cannula attached to it. On the front wall of the holding device, on the side facing the receiving space, there is a cylinder-shaped recess with a radial distance from the cannula, into which recess the open end area of an inner-tube valve is inserted and held. The front wall of the holder is formed without discontinuities except for the receiving opening for the cannula.

U.S. Pat. No. 3,585,984 A discloses another holding device with a double-ended cannula held directly on the front wall. The distal end area in which the cannula is held is formed in a stepped manner in the direction towards the opposite open end. An inner-valve insert with its lip-shaped, circumferential projection is clamped in a cylindrical partial section. Here, too, the front wall of the holder is formed without discontinuities except for the receiving opening for the cannula.

DE 203 01 575 U1 describes a blood-taking device with a holder exhibiting a cannula. In a front end of the guide jacket that can be turned towards a patient, a ring-shaped lip with a threaded section is arranged into which the cannula and a cannula holder receiving it is screwed. The end of the cannula extending into the internal space of the holder is encased by an elastic, hose-like valve rubber. The valve rubber has a collar at its open end that is mounted in a chamber space of the guide jacket and that presses and holds the cannula holder with the external thread against a flange protruding in the radial direction towards the longitudinal axis.

DE 10 2007 031 799 B3 discloses a cannula device for taking spinal cord fluids. A cannula is held directly in a front wall of the holder. The partial section of the cannula protruding into the internal space of the holder is covered by a protective cap. In order to keep it held against the front wall, the protective cap is inserted in a tube-shaped projection extending from the front wall into the internal space. Here, too, the front wall of the holder is formed without discontinuities except for the receiving opening for the cannula.

DE 2 028 662 A and U.S. Pat. No. 3,734,080 A describe a handling device for medical technology that comprises a holder for receiving vacuum containers and a needle device screwed into the holder. The needle device has a double-ended cannula with a holding projection between the two cannula ends. The holding projection has an external thread by means of which it can be screwed into a threaded hole in the front wall of the holder. The partial section of the cannula protruding into the receiving space of the holder is covered by an elastically deformable and perforable closing cap. The closing cap is attached either to only the partial section of the cannula protruding into the receiving space of the holder or to the holding projection. The open end of the closing cap can be partially put over the holding projection.

Another, similarly designed handling device for drawing blood is described in DE 2 908 817 A. It comprises a hollow cylindrical holder in which a first end of a needle device with a double-ended hollow needle is arranged and of which the other, second end is open and designed to receive a blood sample tube. A separate needle holder with an external thread is attached to the double-ended hollow needle. The holder has a threaded hole on its first end to receive and attach the needle holder. The part of the hollow needle protruding into the interior space of the holder is surrounded by a protective sleeve of easily perforable, soft material. The protective sleeve is attached to the needle holder of the screwable needle device.

WO 95/16395 A1 and U.S. Pat. No. 5,897,508 A also describe holding devices for blood sample tubes. The hollow cylindrical holder has a separate needle holder attached to its front wall by a plate-like carrier part. A tube-shaped needle carrier extends from the carrier part and has attached to it by a retaining collar the elastically deformable inner-tube valve. The inner-tube valve covers the cannula held in the needle carrier.

The disadvantage of all these holding devices is that the protective sleeve or inner-tube valve is always attached to the hollow cylindrical holder by another intermediate component.

SUMMARY OF THE INVENTION

The present invention aims to create a handling device and a method for production thereof in which, during production, process safety can be increased and possible downtimes reduced or even avoided entirely. In addition, production is to be simplified for such single-use products that are produced in large quantities.

The aim of the invention is achieved in that the cannula is connected directly to the front wall of the main body part or that the cannula is formed on the front wall as an integrated part of the main body part and the at least one holding element has a retaining protuberance arranged on the holding arm and protruding in the direction towards the longitudinal axis and that in a projection section in the front wall seen in the axial direction the at least one holding element has a perforation through the front wall next to it in the radial direction towards the longitudinal axis, and a cross-section of the perforation in the axial direction is equal to at least one projection area of the retaining protuberance.

The surprising advantage obtained by this is that it allows a directed bearing of the holding element on the outside of the sleeve wall to be achieved. In addition, depending on its design, the provision of the holding arm can achieve the built-up retaining force in this way. This can be designed in a positive and/or force-closed manner based on friction. The provision of the at least one perforation makes it easier to shape the at least one holding element from a technical point of view. In this way complicated designs in the injection mold can be omitted because the opening movement can be executed by a simple up and down movement to create the hollow space inside the form. The injection mold can be designed more simply and operated at greater output because of fewer shifting movements.

The direct connection of the cannula with the front wall allows additional connecting parts that would otherwise be arranged on the cannula to be omitted. An additional simplification of the assembly process can also be achieved if the cannula is pressed into a receiving opening formed in the region of the front wall. This allows several process steps for the connection process to be omitted. It allows pre-treatment of the parts to be connected, allotment of adhesive, and subsequent hardening to be omitted. This can significantly increase process safety for the production process. In addition, if the cannula is formed on the front wall as an integrated part of the main body part, separate formation of the cannula and its connection process with the main body part can be omitted. The majority of the handling device can thus be produced in one work process, in particular in an injection molding process, in a single-part component except for the arrangement of the sleeve as an inner-tube valve. Skipping these process steps allows the systems for joining the main body part to the cannula to be omitted. The omission of the additional system parts allows acquisition costs and operating costs to be saved.

Thus no additional part need be supplied to hold and attach the sleeve. This way production can take place using injection molding without additional demolding steps using a simple injection molding tool, as undercuts in this area are avoided. By the arrangement or provision of at least one holding element on the front wall, the relative fixing of the position of the sleeve in the region of the front wall can be achieved. Because the at least one holding element bears externally on the sleeve, either a force-closed and/or positive connection can be created between the sleeve and the front wall. In this way, the axial position of the sleeve can be fixed and any unintended pulling away of the sleeve from the front wall prevented.

Another possible embodiment has the features that the holding device has a roughly cylindrical or frustum-shaped centering projection which is an integrated part of the front wall and the centering projection protrudes into the open distal sleeve end of the sleeve. As the centering projection is arranged or formed as a single piece directly on the hollow main body part, in particular its front wall, the sleeve can easily be placed on it or put over it. In addition, the centering projection can also act as a counter-holder or counter-stopper for the at least one holding element.

Another preferred embodiment is characterized in that the at least one holding element is arranged at a radial distance while forming a gap from the centering projection. This way a form can be set in a simple injection molding process and shaping can be executed quickly and easily without additional slider movements.

It is further advantageous if the radial distance between the at least one holding element and the centering projection when the holding element is bearing on the sleeve has a value within a range whose lower limit is 5% and whose upper limit is 95% of the non-deformed wall thickness of the sleeve. In this way, the choice of gap width can achieve a deformation of the sleeve wall in the contact area with the holding element and thereby build up a clamping force. This can, on the one hand, create a retaining force between the internal surface of the sleeve and the centering projection and, on the other hand, create a mechanically acting retaining projection between the latter and the holding element by deforming the sleeve wall.

Another possible embodiment has the features that at least the retaining protuberance of the at least one holding element bears on the contact area of a sleeve wall of the sleeve. Thus the clamping force for the sleeve between the retaining protuberance and the centering projection can be established depending on the pressure exerted by the retaining protuberance.

Another design provides for the retaining protuberance to be arranged at a distance from the front wall in the axial direction. In this way a certain overlap area or protrusion of the contact area from the front wall can be achieved. In addition, the protrusion allows a certain safety area to be created within which the sleeve must be fitted to the centering projection in the axial direction. Even if the sleeve pulls away a little or is not entirely fitted to the centering projection, the sleeve can still be held on the centering projection in the axial direction by the at least one holding element.

A possible further development provides that the perforation through the front wall is formed between the holding arm of the at least one holding element and the centering projection. In this way, complicated designs of the injection mold in the area of the front wall can be omitted even in the presence of the centering projection.

Another preferred embodiment is characterized in that, in the region of its open distal sleeve end, the sleeve has a lip protruding beyond the sleeve in the radial direction. The lip protruding radially beyond the sleeve allows an additional retaining element to be created on the sleeve. This also allows the rigidity of the sleeve in its open, distal sleeve end to be increased.

It is further advantageous if the retaining protuberance of the at least one holding element engages behind the lip of the sleeve at its side that faces the open proximal end of the main body part. In this way, the engagement of the retaining protuberance behind the lip additionally creates a positive retaining element for the sleeve in the region of the holding device. This can further improve the retaining force of the holding device.

Another embodiment is characterized in that the at least one holding element can be displaced, in particular rotated, on the front wall. The rotating arrangement and mounting of the at least one holding element make the fitting movement of the sleeve on the centering projection easier. In addition, however, this can achieve an automatic attachment of the sleeve to the centering projection through the automatic return of the at least one holding element into its holding position. This makes it easier to assemble the sleeve on the hollow cylindrical main body part.

Another possible embodiment has the features that the cannula directly connected to the front wall of the main body part is pressed into a receiving opening formed in the region of the front wall, allowing the assembly process to be simplified further. This allows several process steps for the connection process to be omitted. It allows pre-treatment of the parts to be connected, allotment of adhesive, and subsequent hardening to be omitted. This can significantly increase process safety for the production process.

Another design provides for both the receiving opening for the cannula and the centering projection for the sleeve to be arranged on the longitudinal axis. In this way a central arrangement of the cannula and the sleeve within the receiving space of the hollow cylindrical main body part can be achieved.

Another embodiment is characterized in that the cannula is formed on the centering projection as an integrated part of the main body part. In this way the separate formation of the cannula and the process of connecting it to the main body part can be omitted. The majority of the handling device can thus be produced in one work process, in particular in an injection molding process, in a single-part component except for the arrangement of the sleeve as an inner-tube valve. Skipping these process steps allows the systems for joining the main body part to the cannula to be omitted. The omission of the additional system parts allows acquisition costs and operating costs to be saved.

Another preferred embodiment is characterized in that on the front wall on the side facing away from the receiving space a connecting piece is formed that protrudes beyond the front wall in the axial direction. This creates the possibility of coupling and/or connecting the handling device to a great variety of additional parts. Depending on the design of the connecting piece, a great variety of connection and/or coupling options can be created.

Another embodiment is characterized in that the cannula at least partially extends into the connecting piece with its distal cannula end. This extension allows a better hold and therefore greater clamping length of the cannula in the main body part to be achieved.

Another possible embodiment has the features that the cannula protrudes beyond the connecting piece in the axial direction with its distal cannula end and has a penetrating end at its distal cannula end for penetrating into a body part. In a double-ended cannula, this creates the possibility of using the handling device directly without arrangement of additional parts for taking or collecting bodily fluids, in particular blood.

Another design provides for an adapter to be positioned on the connecting piece and at least one airtight section to be formed between the connecting piece and the adapter. The additional option of arranging an adapter piece on the connecting piece and keeping it positioned there further increases the universal possible applications of the handling device. Because of the internal two-way sealing, leaked out outside air can be prevented from being sucked in during the sample-taking process with an evacuated sample container. In addition, however, one of the airtight sections can also form a centering section.

Irrespective of this, the aim of the invention can also be achieved by a method for production of a handling device that consists of executing the following steps:

Formation of a hose-like, elastically deformable and perforable sleeve with an open distal sleeve end and a closed proximal sleeve end;

Formation of a hollow main body part with a distal end at least partially closed by a front wall and an open proximal end, in which the main body part and the front wall define a receiving space, and the proximal end acts to receive at least one partial section of a receiving container in the receiving space, wherein a longitudinal axis (7) extends between the distal end and the proximal end;

Formation of a holding device for the sleeve directly in the region of the front wall on the side facing the receiving space, wherein the holding device is formed by at least one holding element formed on the front wall or arranged on the front wall, wherein the at least one holding element is formed by a holding arm protruding from the front wall;

Formation of a retaining protuberance on the holding arm of the at least one holding element, wherein the retaining protuberance is formed protruding in the direction towards the longitudinal axis;

Formation of a perforation through the front wall, wherein the perforation, seen in a projection section of the at least one holding element in the axial direction, is formed next to it in the radial direction towards the longitudinal axis and a cross-section of the perforation in the axial direction is formed with a projection area equal to at least one projection area of the retaining protuberance;

Arrangement and connection of a needle device formed as a cannula directly with the front wall of the main body part or formation of a needle device formed as a cannula on the front wall of the main body part as an integrated part such that the cannula protrudes into the receiving space with its proximal cannula end starting from the front wall;

Placement of the sleeve with its open distal sleeve end in the region of the at least one holding element formed on the front wall or arranged on the front wall and therefore coverage of the cannula extending into the receiving space;

Production of a contact area between the holding element and the sleeve in which the holding element bears externally on the sleeve.

The advantage of the process steps chosen here is that they allow a directed bearing of the holding element on the outside of the sleeve wall to be achieved. In addition, depending on its design, the provision of the holding arm can achieve the built-up retaining force in this way. This can be designed in a positive and/or force-closed manner based on friction. The provision of the at least one perforation makes it easier to shape the at least one holding element from a technical point of view. In this way complicated designs in the injection mold can be omitted because the opening movement can be executed by a simple up and down movement to create the hollow space inside the form. The injection mold can be designed more simply and operated at greater output because of fewer shifting movements.

Thus no additional part need be supplied to hold and attach the sleeve. This way production can take place using injection molding without additional demolding steps using a simple injection molding tool, as undercuts in this area are avoided. By the arrangement or provision of at least one holding element on the front wall, the relative fixing of the position of the sleeve in the region of the front wall can be achieved. Because the at least one holding element bears externally on the sleeve, either a force-closed and/or positive connection can be created between the sleeve and the front wall. In this way, the axial position of the sleeve can be fixed and any unintended pulling away of the sleeve from the front wall prevented.

Also advantageous is a variation of the method in which, as an additional part of the holding device on the front wall, a roughly cylindrical or frustum-shaped centering projection is formed as an integrated part of the front wall, which centering projection is formed to extend into the open distal sleeve end of the sleeve. As the centering projection is arranged or formed as a single piece directly on the hollow main body part, in particular its front wall, the sleeve can easily be placed on it or put over it. In addition, the centering projection can also act as a counter-holder or counter-stopper for the at least one holding element.

Another preferred procedure provides that the at least one holding element is arranged at a radial distance while forming a gap from the centering projection. This way a form can be set in a simple injection molding process and shaping can be executed quickly and easily without additional slider movements.

Also advantageous is a method in which the perforation through the front wall is formed between the holding arm of the at least one holding element and the centering projection. In this way, complicated designs of the injection mold in the area of the front wall can be omitted even in the presence of the centering projection.

Another method is characterized in that, in the region of its open distal sleeve end, the sleeve is formed with a lip protruding beyond the sleeve in the radial direction. The lip protruding radially beyond the sleeve allows an additional retaining element to be created on the sleeve. This also allows the rigidity of the sleeve in its open, distal sleeve end to be increased.

Also advantageous is a variation of the method in which a gap is formed between the at least one holding element and the centering projection of a distance larger than the wall thickness of the sleeve before the sleeve is placed over the centering projection and, after the sleeve is moved into the gap, the at least one holding element is shifted in the direction towards the longitudinal axis and therefore brought to bear externally on the sleeve in the contact area. This makes it easier to place the sleeve on the centering projection. In addition, this allows the necessary bearing of the at least one holding element and/or the creation of the retaining force of the holding elements to be individually adapted to the formation of the sleeve. The displacement of the at least one holding element to create the retaining force of the sleeve can be executed by a reshaping process of the at least one holding element. Thus, it would be possible to raise the temperature accordingly and soften the material forming the holding element so much that it can be reshaped without breaking in order to bear externally on the sleeve.

BRIEF DESCRIPTION OF THE DRAWINGS

Other objects and features of the invention will become apparent from the following detailed description considered in connection with the accompanying drawings. It is to be understood, however, that the drawings are designed as an illustration only and not as a definition of the limits of the invention.

In the drawings.

DETAILED DESCRIPTION OF PREFERRED EMBODIMENTS

In introduction, let it be noted that in the variously described embodiments, identical parts are provided with identical reference signs or identical part names, and that the disclosures contained in the description as a whole can be carried over analogously to identical parts with identical reference signs or identical part names. Likewise, positional information selected in the description, e.g. above, below, on the side, etc. refer to the directly described and depicted figure and if the position is changed, this positional information carries over analogously to the new position. The term "in particular" is used below to refer to a potentially more specialist design or more detailed specification of an object, which need not necessarily constitute a mandatory, preferred embodiment.

Figure 1:
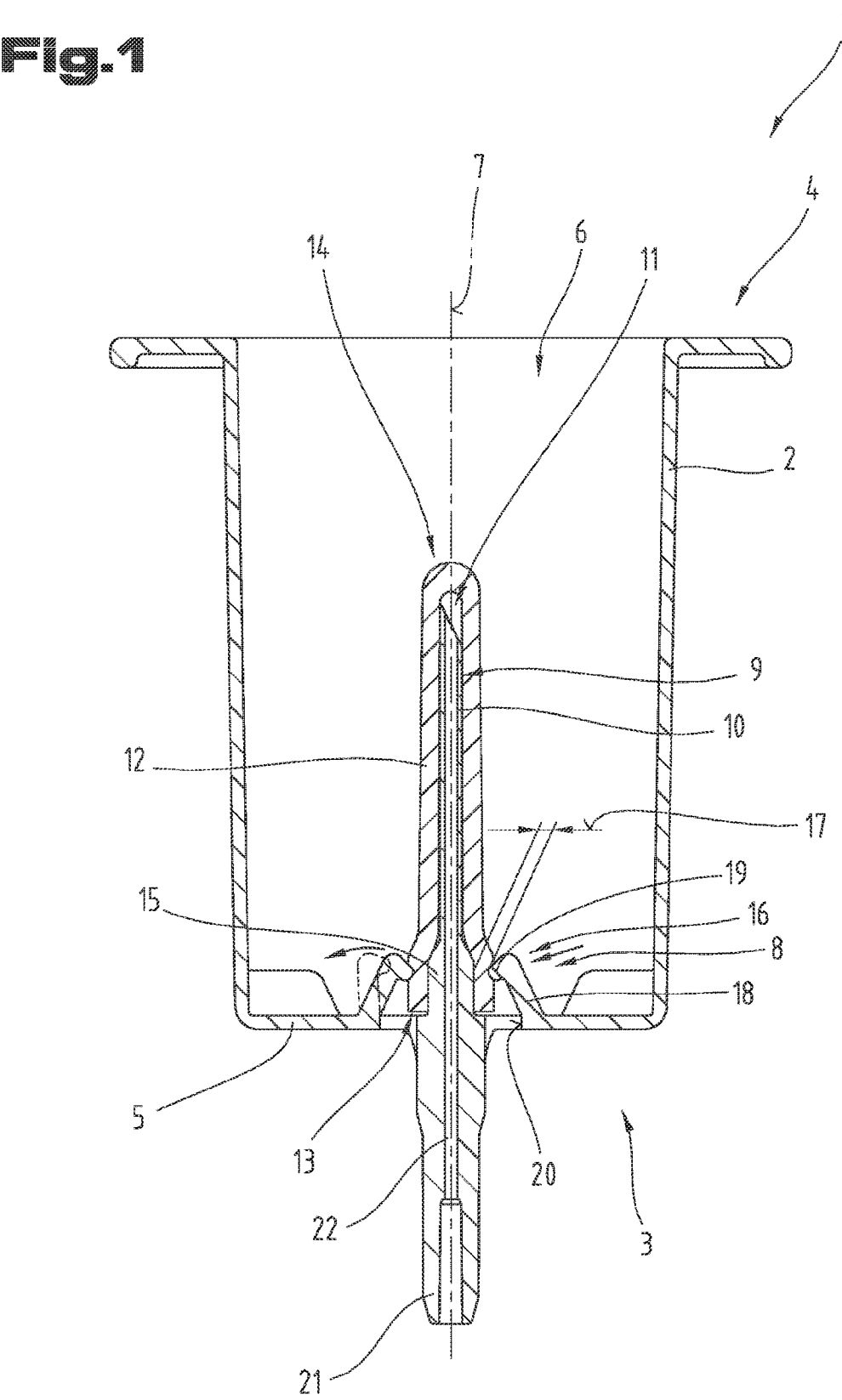
FIG. 1 A first possible formation of the handling device, in axial section.

FIG. 1 shows a first example embodiment of a handling device 1 for a medical assembly, in particular for use in medical technology. Handling device 1 can be used to take or collect bodily fluids, in particular blood, urine, and/or to deliver medications into the body. Handling device 1 is formed such that it can be connected, in particular coupled, to a great variety of medical tools in one end region and at the other end region is formed for receiving at least part of a receiving container not described in further detail here, which receiving container can also be depicted as a blood sample tube or blood collection tube. In such receiving containers, their internal space can also be reduced to a pressure that is lower than the ambient pressure. This can also be called a vacuum tube.

In this example embodiment, the handling device 1 in turn comprises a hollow main body part 2 that has a distal end 3 and a proximal end 4. The main body part 2 can be formed to be roughly tube-shaped and can also be called a holder with a holder wall. Furthermore, a great variety of cross-sectional dimensions and cross-sectional shapes can apply, with these being chosen depending on the dimensions of the receiving container to be received. A light, conical form with or without increments is also possible.

In the present example embodiment, the distal end 3 is at least partially closed by a front wall 5. The main body part 2 with its container wall and the front wall 5 bound or define a receiving space 6. The dimensions of the proximal end 4 are formed in order to be able to receive the previously described partial section of the receiving container in the receiving space 6. In addition, a longitudinal axis 7 extends between the distal end 3 and the proximal end 4. In the region of the open proximal end 4, a handle in the form of a lip-shaped projection but not described in more detail is usually arranged or formed.

It is also shown here that in the region of the front wall 5, on its side that faces the receiving space 6, a holding device 8 for a protective sleeve is arranged which will be described below.

The handling device 1 further comprises a needle device 9, which is formed as a cannula 10. In the present example embodiment, a cannula 10 means a hollow needle which defines or forms in its interior a preferably continuous throughflow channel.

In this example embodiment, the cannula 10 extends from the front wall 5 into the receiving space 6 of the main body part 2 with its proximal cannula end 11. The cannula 10 is further coupled to the main body part 2, in particular its front wall 5.

Coupled is understood here to mean that the cannula 10 is held or arranged on the main body part 2 in the region of its front wall 5. To do this, the cannula 10 can be formed of a separate, independent part that is connected to the main body part 2. This form is shown and described in the following FIGS. 2 to 4.

On the other hand, however, it would also be possible, as shown in FIG. 1, for the cannula 10 to be formed as an integrated part of the main body part 2. The main body part 2 is preferably formed with its front wall 5 as a single-piece part in an injection molding process, usually of a diaphanous to transparent plastic material. It would also be possible to produce the main body part 2 with its front wall 5 of a first material and the cannula 10 of a different second material in the form of a co-injection molding process. This creates the possibility of creating a basic body without additional subsequent joining processes, in which a production process can simultaneously form the cannula 10 as well.

To avoid stab wounds or undesired loss of bodily fluids, in particular blood, from the proximal cannula end 11 of the cannula 10, a hose-like, elastically deformable and perforable sleeve 12 can be provided in a known matter. The sleeve 12, also called an inner-tube valve, has an open distal sleeve end 13 and a closed proximal sleeve end 14. The material of the sleeve 12 is preferably chosen to be a perforable, self-closing material, as has been sufficient thus far.

The holding device 8 described above acts to keep the sleeve 12 positioned in the region of the front wall 5. The holding device 8 can comprise a roughly cylindrical or frustum-shaped centering projection 15 formed directly on the front wall 5. Then the centering projection 15 is also a direct, integrated part of the front wall and therefore of the main body part 2.

The open distal sleeve end 13 is placed on the centering projection 15 and therefore arranged or held on it. Thus the centering projection 15 extends into the open distal sleeve end 13 of the sleeve 12. As the material of sleeve 12 is elastically deformable, full contact, in particular a press fit, is chosen between the centering projection 15 and the open distal sleeve end 13. This is achieved by elastic widening of the distal sleeve end 13, as shown in a simplified depiction. Furthermore, in this position of the sleeve 12 the proximal cannula end 11 of the cannula 10 is covered by the closed proximal sleeve end 14 of the sleeve 12.

The holding device 8 further comprises at least one, preferably several, holding elements 16 for the sleeve 12 formed on the front wall 5 or arranged on the front wall 5. The holding elements 16 are typically arranged evenly around the circumference, with their number typically numbering between two and eight and potentially more. The at least one holding element 16 is arranged on the side of the front wall 5 facing the receiving space 6 and at a radial distance from the centering projection 15, forming a gap 17. The gap 17 acts to receive a sleeve wall of the sleeve 12, to in this way bring about a relative positioning and/or mounting of the sleeve 12 on the centering projection 15 when in the fully joined condition. Herein the at least one holding element 16 bears externally on a contact area of the sleeve 12. This is shown in simplified form by a deformation in the contact area of the holding elements 16 on the sleeve 12. Herein the radial distance for forming the gap 17 between the at least one holding element 16 and the centering projection 15 when the holding element 16 is bearing on the sleeve 12 can have a value within a range whose lower limit is 5% and whose upper limit is 95% of the non-deformed wall thickness of the sleeve 12 in this region. The lower the width of the gap 17, the higher the achieved pressure on the centering projection 15 and the associated deformation of the sleeve 12, in particular its sleeve wall.

It is further shown here that the at least one holding element 16 has a holding arm 18 protruding from the front wall 5 and a retaining protuberance 19 protruding on the holding arm 18 in the direction towards the longitudinal axis 7 and therefore towards the centering projection 15. Herein at least the retaining protuberance 19 of the at least one holding element 16 bears externally on the contact area of the sleeve wall of the sleeve 12. The extent of the clamping of the sleeve 12 between the centering projection 15 and the at least one holding element 16 can be determined depending on the gap width of the gap 17 chosen. In order to form a spring arm formed by the at least one holding arm 18, the retaining protuberance 19 can be arranged at a distance from the front wall 5 in the axial direction.

For easier production and demolding of the handling device 1, in particular its holding device 8, using a simple opening process of the injection mold, it is further provided here for the front wall 5 to have a perforation 20 through the front wall 5 formed or arranged between the at least one holding element 16, in particular its holding arm 18, and the centering projection 15. The same number of perforations 20 as the number of holding elements 16 should be chosen. The perforation 20 extends from the edge region of the holding arm 18 of the holding element 16 at least so far in the direction towards the longitudinal axis 7 that the front most and thus the edge region of the retaining protuberance 19 that faces the longitudinal axis 7 aligns axially with the perforation 20. The size and/or cross-section of the perforation 20 equals at least a projection area of the retaining protuberance 19 in the axial direction and, where necessary, a part of the holding arm 18 if it happens to be in an inclined position. In this way, a simple opening movement can demold the handling device 1 out of a forming mold not described in further detail.

To avoid direct contact of the receiving container to be received in the receiving space 6, in particular of its closing device, with the holding elements 16 of the holding device 8, distancing elements not described in more detail can be arranged or formed on the inside of the front wall 5 facing the receiving space 6. These can be formed by partitions and/or ribs that prevent the receiving container from being pushed further in than until it makes contact and thus rests on the distancing elements. This can, on the one hand, prevent damage to the holding elements 16 and, on the other hand, create sufficient space for the sleeve 12 to deform while the cannula 10 pierces through the closing device of the receiving container.

In the example embodiment given here, the main body part 2 with the front wall 5 and the holding device 8 together with the cannula 10 forms a connected component made of a material that can be processed by an injection molding process. Thus the cannula 10 is arranged and formed directly on the centering projection 15 as an integrated part.

It is further shown here that a connecting piece 21 that protrudes beyond the front wall 5 in the axial direction can be arranged, in particular formed, on the front wall 5 on the side facing away from the receiving space 6.

To allow throughflow between the distal end piece of the connecting piece 21 and the proximal cannula end 11 of the cannula 10, a flow channel 22 extends continuously between these parts. The flow channel 22 is thus formed within the connecting piece 21 and the centering projection 15 in the region of the front wall 5 until the hollow cannula 10.

The external bearing of the holding element 16 on the sleeve 12 in the previously described contact area can be executed in different ways.

A first possibility would be to arrange the holding element 16, in particular its holding arm 18, in a position relative to the centering projection 15 such that the distance and thus gap width of the gap 17 effect a secure hold and clamping of the sleeve 12 by the holding element 16 on the centering projection 15 in the contact area. The elastic widening and shift of the holding element 16, in particular its holding arm 18, on the side facing away from the longitudinal axis 7 allows the sleeve 12 to be placed on and positioned with its distal sleeve end 13 on the centering projection 15. Elastic springing back or setting back of the at least one holding element 16, in particular its holding arm 18, then clamps the sleeve 12 onto the centering projection 15. The shifted position of the holding element 16 is indicated in the left part of the holding device 8 by dotted lines.

A second possibility would be to choose the distance and thus the gap width of the gap 17 by appropriate arrangement of the at least one holding element 16, in particular its holding arm 18, such that an unhampered placement on, especially pushing on, of the open distal sleeve end 13 onto the centering projection 15 is allowed. After this a corresponding reshaping process reshapes/deforms the at least one holding element 16, in particular its holding arm 18, in the direction towards the longitudinal axis 7 to the extent that it, in particular its retaining protuberance 19, is brought to bear externally on the contact area of the sleeve 12. This is shown in a simplified manner by an arrow in the right part of the holding device 8. The already deformed position of the holding element 16 is only shown in the right part here. The non-deformed initial position could be as shown by dotted lines in the left part of the holding device 8.

Figure 2:
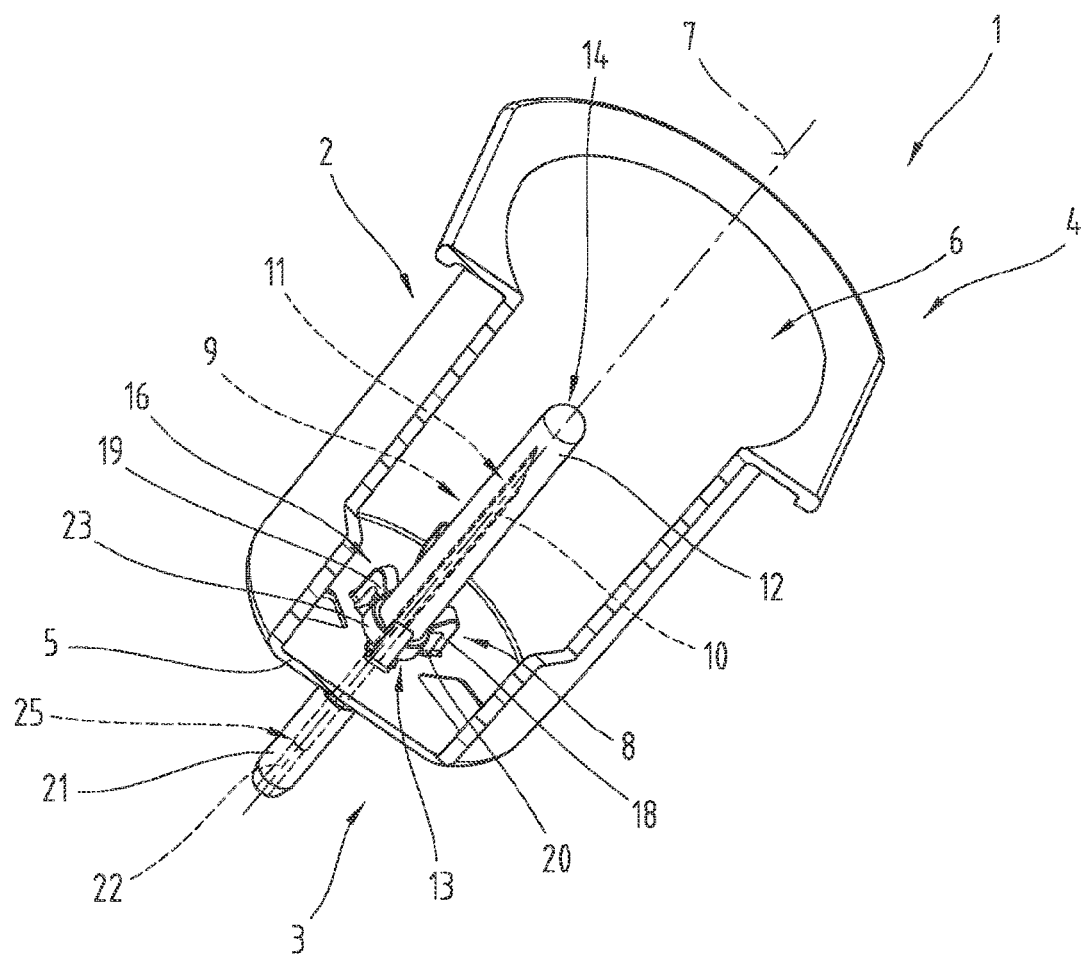
FIG. 2 A second embodiment of the handling device, in an axial partial section and schematic depiction.
Figure 3:
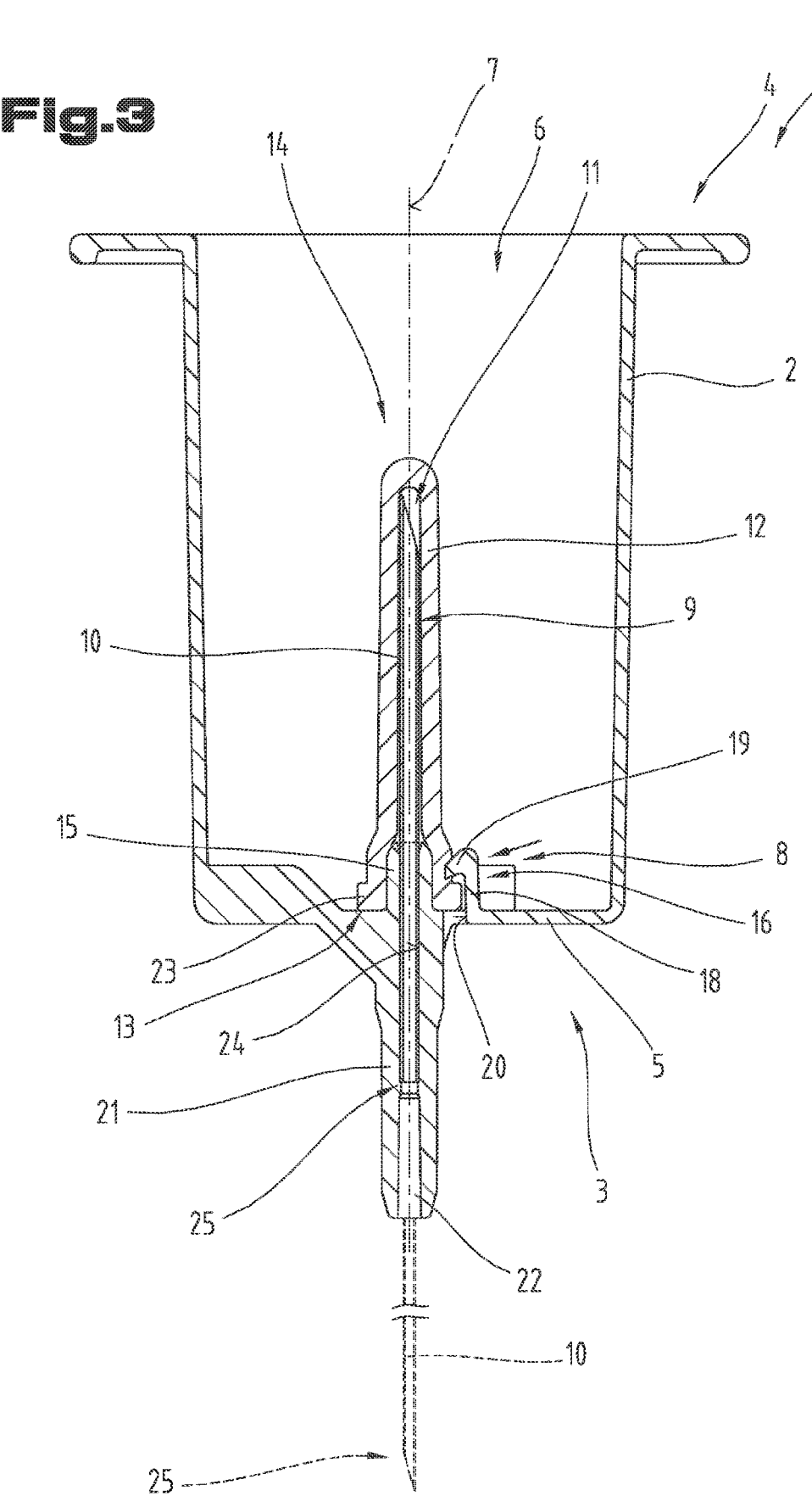
FIG. 3 The handling device as in FIG. 2, in axial section.

FIGS. 2 and 3 depict another, potentially independent embodiment of the handling device 1, where once again the same reference signs and part names are used for the same parts as have been used in the preceding FIG. 1. To avoid unnecessary repetition, please refer to the detailed description in the above FIG. 1.

The embodiment of the handling device 1 shown here also comprises the main body part 2 with its distal end 3 closed by the front wall 5 and the open proximal end 4. The longitudinal axis 7 extends between these two ends 3, 4. The centering projection 15 is likewise a direct, integrated part of the front wall 5 and protrudes from it into the receiving space 6. It is additionally shown here that, in the region of its open distal sleeve end 13, the sleeve 12 has a lip 23 protruding beyond the sleeve 12 in the radial direction. In the present embodiment, the lip 23 acts as a positive connection means and/or holding means together with the holding device 8, in particular its at least one holding element 16. To achieve reciprocal positive engagement, the retaining protuberance 19 of the at least one holding element 16 can engage behind the lip 23 of the sleeve 12 at its side that faces the open proximal end 4 of the main body part 2.

As described above, the engagement and external bearing on the sleeve 12 can be analogous, as described in detail above in FIG. 1. It would further be possible in this embodiment for the retaining protuberance 19 to only engage behind the lip 23 and exert no further pressure on the sleeve wall of the sleeve 12 and not cause the previously described deformation of the sleeve 12, in particular its sleeve wall. However, it would also be possible to reshape the holding element 16, in particular its holding arm 18, in its position in order to hold the sleeve 12. This can be achieved by e.g. a thermal reshaping process.

In the contrast to the previously described embodiment depicted in FIG. 1, it is shown here that the cannula 10 is formed by a separate part, in particular of a metallic material. A lasting, airtight connection must be formed between the cannula 10 and the main body part 2, in particular its front wall 5. Therefore it is provided here for a corresponding receiving opening 24 to be formed on the front wall 5 of the main body part 2. The cannula 10 is inserted directly into this receiving opening 24. If the connecting piece 21 described above is again provided, the receiving opening 24 can also at least partially extend into it. The receiving opening 24 can also be arranged in the centering projection 15. Depending on the desired clamping length of the cannula 10, the receiving opening 24 can have a larger internal dimension than the cannula dimension in the region of the centering projection 15. This makes it easier to insert or introduce the cannula 10 into the receiving opening 24.

In order to dispense with additional connection means such as adhesives or the like, the cannula 10 can be pushed into the receiving opening 24 formed in the region of the front wall 5. To avoid outside air from being sucked into this region, attention should be paid to making an airtight pressure-fit connection between the outside of the cannula 10 and the main body part 2, in particular its front wall 5. This simple process step allows additional process steps such as applying and hardening additional adhesives to be omitted. This can ensure greater process safety and avoid accompanying contamination of the contact by adhesive residues or handling devices 1 that are unusable because of adhesive bonds that are not airtight.

To achieve central placement and positioning of the cannula 10 in regard to the main body part 2, it can be advantageous if both the receiving opening 24 for the cannula 10 and the centering projection 15 for the sleeve 12 are each arranged to lie on the shared longitudinal axis 7.

The cannula 10 in turn also has a distal cannula end 25. The distal cannula end 25 extends at least into the centering projection 15 and potentially into the front wall 5. If the connecting piece 21 is also present, the cannula 10 can extend at least partially into the connecting piece 21 with its cannula end 25.

Irrespective of this, however, it would also be possible to form the cannula 10 with a greater lengthwise extension as depicted in dotted lines in FIG. 3. Then the cannula 10 can extend beyond the connecting piece 21 with its distal cannula end 25 in the axial direction. In addition, at its distal cannula end 25 the cannula 10 can have a piercing end for piercing a body part not shown in further detail. The piercing end is typically formed by beveling on the cannula 10.

Figure 4:
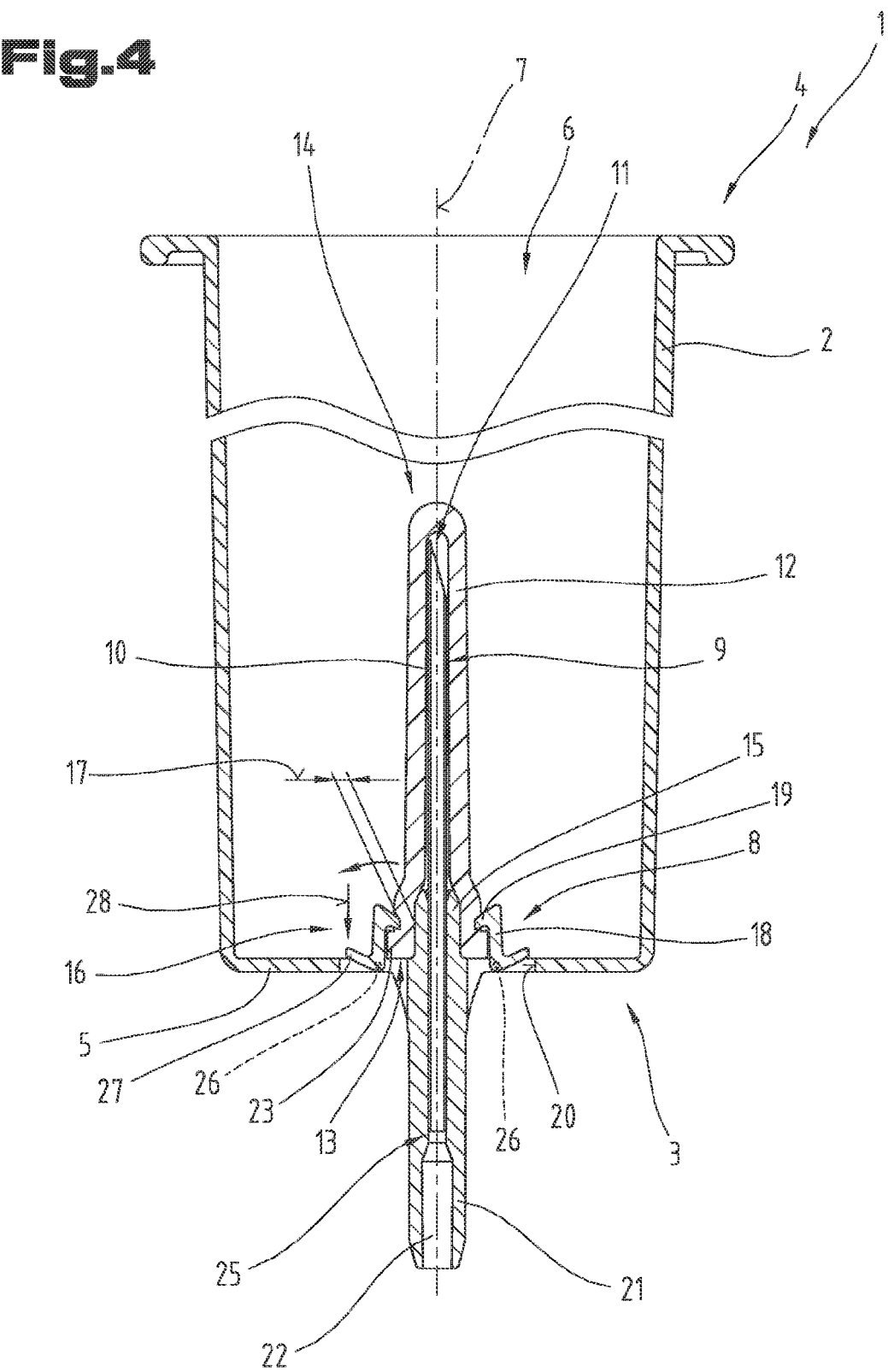
FIG. 4 A third possible formation of the handling device, in axial section.

FIG. 4 depicts another, potentially independent embodiment of the handling device 1, where once again the same reference signs and part names are used for the same parts as have been used in the preceding FIGS. 1 to 3. To avoid unnecessary repetition, please refer to the detailed description in the above FIGS. 1 to 3.

In the example embodiment of the handling device 1 shown here, it also comprises the main body part 2 with its distal end 3 closed by the front wall 5 and the open proximal end 4. The centering projection 15 is again arranged in the region of the front wall 5 and is likewise a direct, integrated component of the front wall 5. The sleeve 12 is placed on the centering projection 15 as has already been described above.

In this example embodiment as well, in the region of its open distal sleeve end 13 the sleeve 12 has a lip 23 protruding beyond the sleeve 12 in the radial direction. Here, too, the lip 23 acts as a positive connection means and/or holding means together with the holding device 8, in particular its at least one holding element 16.

The cannula 10 is also formed as a separate part, in particular of a metallic material, in this example embodiment. Furthermore, the cannula 10 is again directly connected to the main body part 2, in particular its front wall 5, and, where applicable, to the connecting piece 21 by a press fit. To avoid outside air from being sucked into this region, attention should be paid to making an airtight pressure-fit connection between the outside of the cannula 10 and the main body part 2, in particular its front wall 5.

The holding device 8 again comprises at least the one holding element 16, which in the present example embodiment is arranged on the front wall 5 in a manner that allows it to rotate. The holding element 16 again comprises the holding arm 18 protruding out of the front wall 5, on which the retaining protuberance 19 can be arranged in the direction towards the longitudinal axis 7 and/or the centering projection 15 protruding above it. At its holding arm end that faces the front wall 5, the holding arm 18 is preferably connected to the front wall 5 on both sides by fixed retaining dowels 26. The retaining dowels 26 bridge the free position of the holding arm 18 on both sides in the region of the perforation 20 and each form a sort of torsion bar. This makes it possible to use the retaining dowels 26 to shift the holding arm 18 in its position relative to the front wall 5 elastically and in such a manner that it springs back. The holding arm 18 executes a kind of tilting or pivoting movement around the retaining dowels 26. Because of the presence of the perforation 20, the at least one holding element 16 can again be formed as a single piece on the front wall 5. Since the at least one holding element 16 is again directly on the front wall 5 as an integrated part of it and therefore also of the main body part 2, additional production and joining steps can be omitted. It would, however, also be conceivable for the at least one holding element 16 to be formed by a separate component attached to the front wall 5.

To facilitate the displacement or relative movement of the holding arm 18, e.g. in order to place the sleeve 12 on the centering projection 15, an adjusting arm 27 can be arranged or formed on the holding arm 18 on the side facing away from the centering projection 15 and from the retaining protuberance 19. This adjusting arm 27 can make an angle with the holding arm 18 that is less than 90° on the side facing the receiving space 6. The enclosed angle should preferably be chosen to be between 80° and 50°. Because of this angled placement of the adjusting arm 27 relative to the holding arm 18 and therefore also the front wall 5, at least a partial section of the adjusting arm 27 extends beyond the front wall 5 into the receiving space 6. Usually the holding arm 18 is oriented at a right angle to the front wall 5 in its non-deformed initial position or a parallel orientation relative to the longitudinal axis 7 is chosen.

If a force—as shown by the included arrow 28—is exerted on the adjusting arm 27, the adjusting arm 27 is rotated around the retaining dowels 26 in the direction towards the front wall 5. However, this also rotates the holding arm 18 together with the retaining protuberance 19 on the side facing away from the longitudinal axis 7, causing the gap 17 between the holding arm 18, in particular its retaining protuberance 19, and the centering projection 15 to widen. This makes it easier to place the sleeve 12 on the centering projection 15 even if a lip 23 is arranged upon it.

If the force—as shown by arrow 28—is removed, the holding element 16 automatically springs back to its initial position. Here the lip 23 can again engage through the retaining protuberance 19 on its side facing the open proximal end 4.

Figure 5:
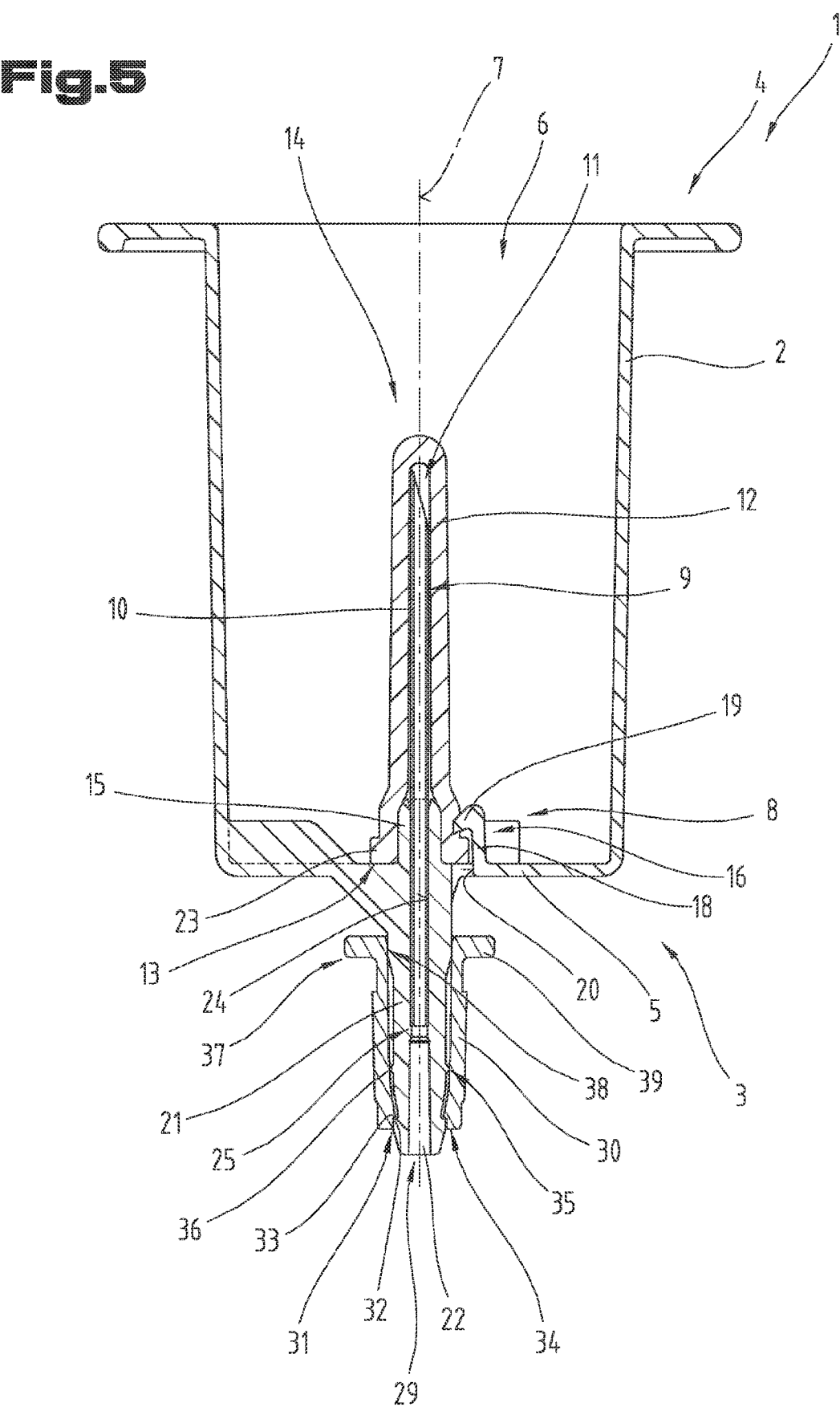
FIG. 5 Another handling device with an adapter arranged in the region of its connecting piece, in axial section.

FIG. 5 depicts another, potentially independent embodiment of the handling device 1, where once again the same reference signs and part names are used for the same parts as have been used in the preceding FIGS. 1 to 4. To avoid unnecessary repetition, please refer to the detailed description in the above FIGS. 1 to 4.

The formation of the holding device 8 and the formation and arrangement of the cannula 10 and of its sleeve 12 can be executed in accordance with one of the embodiments described above. The various depictions of the components described above can also be combined at will into a unit. The additional embodiment described here can be combined with each of the previously described example embodiments.

Seen in axial section, the connecting piece 21 can have a great variety of spatial shapes and cross-sectional shapes and the handling device 1 can thus be adapted to a variety of configurations. If the connecting piece 21 is formed so as to narrow in the direction towards the distal end, membranes, in particular silicon membranes as used for blood bags or plasma bags, can easily be pierced in this way. The external form of the connecting piece 21 can also be formed by a Luer cone commonly used in medical technology, which can also be called a Luer taper and has a cone angle of 6%. In this way a great variety of medical components, such as Luer needles, hose connections, and the like can easily be connected, in particular coupled.

In this example embodiment, the connecting piece 21 has a stepped longitudinal outline when viewed in axial section starting from the front wall 5 through to its distal connecting piece end 29. In this example embodiment, the connecting piece 21 further acts as a coupling piece with an adapter 30. The adapter 30 acts as an intermediate part in order to create, depending on the design of the adapter 30, a connection or coupling opportunity with the connecting piece 21 and therefore with the handling device 1. The adapter 30 can preferably be formed of a different material than the material of the main body part 2 and/or its front wall 5. A clear and/or transparent material, in particular plastic, is preferable for forming the main body part 2 and/or its front wall 5 and the components of the holding device 8 arranged on it. In addition, a hose can be connected either directly to the connecting piece 21 or to the adapter 30. The hose, which is not described in more detail, can also be formed of a plastic, in particular PVC material. Bonding to the connecting piece 21 or the adapter 30 is also possible.

The cannula 10 can be held extending partially into the interior of the connecting piece 21 by an airtight press fit. In addition, the flow channel 22 extends subsequent to the cannula 10 through the center of the connecting piece 21 to the distal open connecting piece end 29 of the connecting piece 21.

To facilitate reciprocal holding and to fix the axial position of the adapter 30 on the connecting piece, a catch device 31 with interacting catch elements 32, 33 is provided. In this example embodiment, the catch device 31 is arranged next to the distal connecting piece end 29. The first catch element 32 formed or arranged on the connecting piece 21 is realized as a circumferential ledge with an undercut in the direction towards the front wall 5. The matching counterpart, namely the second catch element 33, is arranged in the open distal adapter end 34.

A first airtight section 35 can be provided in a middle section of the adapter 30. This first airtight section 35 is formed by an airtight element 36, e.g. in the form of a sealing ring, running around the connecting piece 21 and protruding above the external surface of the connecting piece 21. This airtight element 36 protruding in the radial direction has a decreasing cross-sectional form when viewed in axial section with increasing distance from the longitudinal axis 7.

In this example embodiment, it is further shown that a second airtight section 38 and/or a centering section can be formed or arranged in the region of the proximal adapter end 37. For safety reasons, both airtight sections 35, 38 can be provided, both preferably having an airtight bearing on each other. In this way, outside air can be prevented from being sucked in between the adapter 30 and the connecting piece 21 into the flow channel 22.

It is further shown here that a flange 39 can be arranged or formed in the region of the proximal adapter end 37. The flange 39 can, for example, serve to form a stopper for a hose piece or the like arranged on and held on the outside of the adapter 30. The flange 39 can also serve as a guide and/or for radial orientation, for transport, or for alignment of the adapter 30.

It is further shown here that it can be advantageous if there is a distance between the inner surface of the adapter 30 and the outer surface of the connecting piece 21 between the two airtight sections 35 and 38. This can make it easy to place the adapter 30 on the connecting piece 21 and simply create a secure airtight connection through a pressure fit in at least one of the two airtight sections 35 and/or 38. It should be noted that it is also possible to form or provide only one of the above mentioned airtight sections 35 or 38.

The connecting piece 21 and the adapter 30 locked to it and/or held coupled to it in the axial direction can also be used in all other embodiments described here. The same is true of the cannula 10 protruding beyond the connecting piece 21 in the distal direction.

Figure 6:
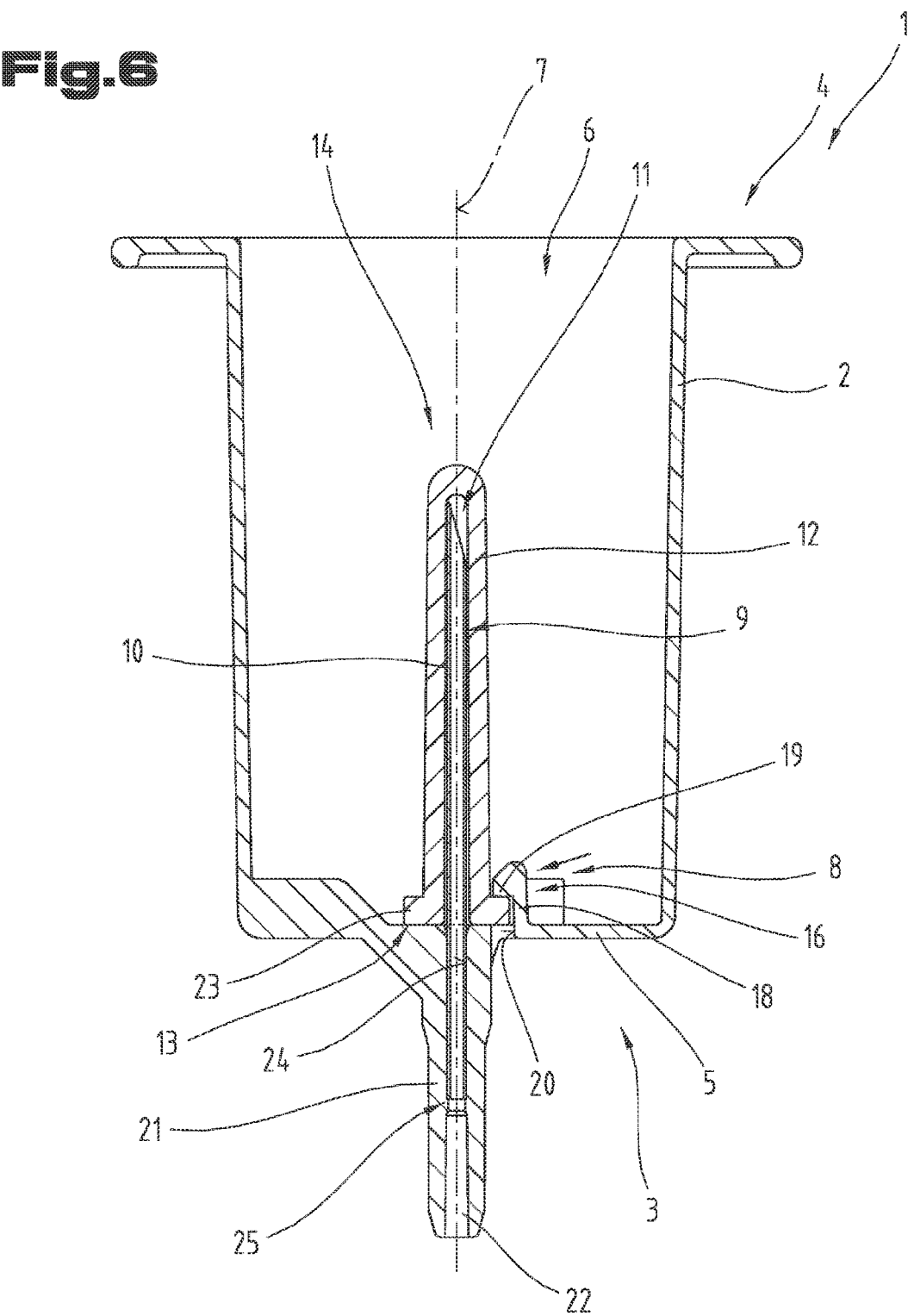
FIG. 6 An additional other possible formation of the handling device, in axial section.

FIG. 6 depicts another, potentially independent embodiment of the handling device 1, where once again the same reference signs and part names are used for the same parts as have been used in the preceding FIGS. 1 to 5. To avoid unnecessary repetition, please refer to the detailed description in the above FIGS. 1 to 5.

As the embodiment shown here is very similar to that in FIGS. 2 and 3, only the details that are different will be discussed.

The embodiment of the handling device 1 shown here also comprises the main body part 2 with its distal end 3 closed by the front wall 5 and the open proximal end 4. The longitudinal axis 7 extends between these two ends 3, 4.

In contrast to the embodiment in FIGS. 2 and 3, here the front wall 5 is roughly even in the region of the sleeve 12 to be placed on it and therefore formed without the previously described centering projection 15. The sleeve 12 can have the lip 23 protruding above the sleeve 12 in the radial direction in the region of its open distal sleeve end 13, but this is not absolutely necessary. In the present embodiment, the lip 23 then acts as a positive connection means and/or holding means together with the holding device 8, in particular its at least one holding element 16. To achieve reciprocal positive engagement, the retaining protuberance 19 of the at least one holding element 16 engages behind the lip 23 of the sleeve 12 at its side that faces the open proximal end 4 of the main body part 2.

As described above, the engagement and external bearing on the sleeve 12 can be analogous, as described in detail above in FIGS. 2 and 3. However, it would also be possible to reshape the holding element 16, in particular its holding arm 18, in its position in order to hold the sleeve 12. This can be achieved by e.g. a thermal reshaping process. Irrespective of this, the at least one holding element 16 could also be formed to rotate and/or be a separate component that is likewise arranged directly on or within the front wall 5 and formed on it as described in FIG. 4. It would also be possible to form the cannula 10 as an integrated part of the front wall 5 or the main body part 2.

Here the cannula 10 is also formed as a separate part, in particular of a metallic material. A lasting, airtight connection must be formed between the cannula 10 and the main body part 2, in particular its front wall 5. In order to dispense with additional connection means such as adhesives or the like, the cannula 10 can be pushed into the receiving opening 24 formed in the region of the front wall 5.

However, it would also be possible for the cannula 10 to be formed directly on the front wall 5 as an integrated part of the main body part; a similar design was described in FIG. 1, though with a centering projection 15.

Here, too, the perforation 20 in the front wall 5 can be arranged or formed in a projection section of the holding element 16 seen in the axial direction and placed next to the latter in the radial direction towards the longitudinal axis 7. This also acts here to shape the at least one holding element 16. The perforation 20 extends from the edge region of the holding arm 18 of the holding element 16 at least so far in the direction towards the longitudinal axis 7 that the front most and thus the edge region of the retaining protuberance 19 that faces the longitudinal axis 7 aligns axially with the perforation 20.

The sleeve 12 lies with its open distal sleeve end 13 on the front wall 5, braced against it in the axial direction, and is held on the front wall 5 by the at least one holding element 16 both in the axial direction and to a certain extent in the radial direction. It is intended to work together with the lip 23.

The production and/or provision and the joining of the individual parts to the handling device 1 can comprise somewhat different process steps depending on the design of the basic body:

Formation of a hose-like, elastically deformable and perforable sleeve 12 with an open distal sleeve end 13 and a closed proximal sleeve end 14;

Formation of a hollow main body part 2 with a distal end 3 at least partially closed by a front wall 5 and an open proximal end 4, in which the main body part 2 and the front wall 5 define a receiving space 6, and the proximal end 4 acts to receive at least one partial section of a receiving container in the receiving space 6, wherein a longitudinal axis 7 extends between the distal end 3 and the proximal end 4;

Formation of a holding device 8 for the sleeve 12 directly in the region of the front wall 5 on the side facing the receiving space 6, wherein the holding device 8 is formed by at least one holding element 16 formed on the front wall 5 or arranged on the front wall 5;

Arrangement and connection of a needle device 9 formed as a cannula 10 with the front wall 5 of the main body part 2 or formation of a needle device 9 formed as a cannula 10 on the front wall 5 of the main body part 2 such that the cannula 10 protrudes into the receiving space 6 with its proximal cannula end 11 starting from the front wall 5;

Placement of the sleeve 12 with its open distal sleeve end 13 in the region of the at least one holding element 16 formed on the front wall 5 or arranged on the front wall 5 and therefore coverage of the cannula 10 extending into the receiving space 6;

Production of a contact area between the holding element 16 and the sleeve 12 in which the holding element 16 bears externally on the sleeve 12.

In the region of its open distal sleeve end 13 the sleeve 12 is preferably formed with a lip 23 protruding beyond the sleeve 12 in the radial direction.

In addition, on the front wall 5 a roughly cylindrical or frustum-shaped centering projection 15 can be formed as an integrated part of the front wall 5 as an additional part of the holding device 8. The centering projection 15 is formed to extend into the open distal sleeve end 13 of the sleeve 12.

It is further possible for the gap 17 formed between the at least one holding element 16 and the centering projection 15 to be formed with a distance greater than the wall thickness of the sleeve 12 before the sleeve 12 is placed on the centering projection 15. After the sleeve 12 is moved into the gap 17, the at least one holding element 16 is moved in the direction towards the longitudinal axis 7 and thus brought to bear externally on the sleeve 12 in the contact area.

The example embodiments show possible variations of the handling device 1; let it be noted at this juncture that the invention is not limited to the specially portrayed variations of embodiments themselves, but that diverse combinations of the individual variations of embodiments are possible and that this possibility of variation falls within the competence of a person active in this technical field based on the teaching regarding technical action provided by this invention.

Furthermore, individual characteristics or combinations of characteristics from the depicted and described various example embodiments can constitute independent inventive or invented solutions.

The aim underlying the independent invented solutions can be taken from the description.

All information regarding ranges of values in this description should be understood to mean that these include any and all partial ranges, e.g. the statement 1 to 10 should be understood to mean that all partial ranges starting from the lower threshold 1 and the upper threshold 10 are included, i.e. all partial ranges begin with a lower threshold of 1 or larger and with an upper threshold of 10 or less, e.g. 1 to 1.7 or 3.2 to 8.1 or 5.5 to 10.

Above all, the individual embodiments shown in FIG. 1; 2; 3; 4; 5; 6 can form the subject of independent invented solutions. The relevant aims according to the invention and solutions can be found in the detailed descriptions of these figures.

As a matter of form, let it be noted that, to facilitate a better understanding of the design of the handling device 1, it and it components have in places been portrayed not to scale and/or enlarged and/or scaled-down.

Although only a few embodiments of the present invention have been shown and described, it is to be understood that many changes and modifications may be made thereunto without departing from the spirit and scope of the invention.

| List of reference signs | |
|---|---|
| 1 | Handling device |
| 2 | Main body part |
| 3 | Distal end |
| 4 | Proximal end |
| 5 | Front wall |
| 6 | Receiving space |
| 7 | Longitudinal axis |
| 8 | Holding device |

| List of reference signs | |
|---|---|
| 9 | Needle device |
| 10 | Cannula |
| 11 | Proximal cannula end |
| 12 | Sleeve |
| 13 | Distal sleeve end |
| 14 | Proximal sleeve end |
| 15 | Centering projection |
| 16 | Holding element |
| 17 | Gap |
| 18 | Holding arm |
| 19 | Retaining collar |
| 20 | Perforation |
| 21 | Connecting piece |
| 22 | Flow channel |
| 23 | Lip |
| 24 | Receiving opening |
| 25 | Distal cannula end |
| 26 | Retaining dowels |
| 27 | Adjusting arm |
| 28 | Arrow |
| 29 | Distal connecting piece end |
| 30 | Adapter |
| 31 | Catch device |
| 32 | Catch element |
| 33 | Catch element |
| 34 | Distal adapter end |
| 35 | First airtight section |
| 36 | Sealing element |
| 37 | Proximal adapter end |
| 38 | Second airtight section |
| 39 | Flange |

The invention claimed is:

1. A handling device comprising:
   (a) a hollow main body part having first and second side walls, a front wall, a distal end at least partially closed by the front wall, an open proximal end, a receiving space defined by the first and second side walls and the front wall, and a longitudinal axis extending between the distal end and the proximal end, wherein the proximal end is configured to receive at least one partial section of a receiving container in the receiving space;
   (b) a needle device comprising a cannula coupled to the main body part and having a proximal cannula end protruding into the receiving space from the front wall;
   (c) a hose-shaped, elastically deformable and perforable sleeve having an open distal sleeve end and a closed proximal sleeve end and covering the proximal cannula end with the closed proximal sleeve end; and
   (d) a holding device formed or arranged directly on the front wall and holding the sleeve in an axial direction, wherein the holding device comprises a plurality of holding elements for the sleeve displaceable on the front wall and arranged on a side of the front wall facing the receiving space and distributed over the circumference, wherein each of the holding elements has a holding arm protruding from the front wall and bears externally on the sleeve in a contact area;
   wherein:
   the cannula is directly connected to the front wall or formed on the front wall as an integrated part of the main body part;
   each of the holding elements has a retaining protuberance arranged on the holding arm and protruding in a direction towards the longitudinal axis;
   in the front wall, in a projection section of each of the holding elements seen in the axial direction, a perforation through the front wall is formed next to each of the holding elements in a radial direction towards the longitudinal axis;

each of the perforations has a cross-section in the axial direction equal to at least one projection area of the retaining protuberance; and the open distal sleeve end of the sleeve is supported in a circumferential direction between the perforations directly against the front wall in the axial direction.

2. The handling device according to claim 1, wherein the holding device has a roughly cylindrical or frustum-shaped centering projection which is an integrated part of the front wall and the centering projection protrudes into the open distal sleeve end of the sleeve.

3. The handling device according to claim 2, wherein each of the holding elements is arranged at a radial distance and forms a gap from the centering projection.

4. The handling device according to claim 3, wherein the radial distance between each of the holding elements and the centering projection when each of the holding elements is bearing on the sleeve has a value within a range whose lower limit is 5% and whose upper limit is 95% of a non-deformed wall thickness of the sleeve.

5. The handling device according to claim 1, wherein at least the retaining protuberance of each of the holding elements bears on the contact area of a sleeve wall of the sleeve.

6. The handling device according to claim 1, wherein the retaining protuberance is arranged at a distance from the front wall in the axial direction.

7. The handling device according to claim 2, wherein the perforation through the front wall is formed between the holding arm of each of the holding elements and the centering projection.

8. The handling device according to claim 1, wherein in a region of the open distal sleeve end, the sleeve has a lip protruding beyond the sleeve in the radial direction.

9. The handling device according to claim 5, wherein the retaining protuberance of each of the holding elements engages behind the lip of the sleeve at a side that faces the open proximal end of the main body part.

10. The handling device according to claim 1, wherein each of the holding elements is displaceable on the front wall.

11. The handling device according to claim 2, wherein the cannula is directly connected to the front wall of the main body part and is pressed into a receiving opening formed in a region of the front wall.

12. The handling device according to claim 11, wherein both the receiving opening for the cannula and the centering projection for the sleeve are arranged to lie on the longitudinal axis.

13. The handling device according to claim 2, wherein the cannula is formed on the centering projection as an integrated part of the main body part.

14. The handling device according to claim 1, wherein on the front wall on a side facing away from the receiving space a connecting piece is formed that protrudes beyond the front wall in the axial direction.

15. The handling device according to claim 14, wherein the cannula at least partially extends into the connecting piece with the distal cannula end.

16. The handling device according to claim 14, wherein the cannula protrudes beyond the connecting piece in the axial direction with the distal cannula end and has a penetrating end at the distal cannula end for penetrating into a body part.

17. The handling device according to claim 14, wherein an adapter is positioned on the connecting piece and at least one airtight section is formed between the connecting piece and the adapter.

18. A method for production of a handling device that comprises the following steps:

forming a hose-shaped, elastically deformable and perforable sleeve having an open distal sleeve end and a closed proximal sleeve end;

forming a hollow main body part having first and second side walls, a front wall, a distal end at least partially closed by the front wall, an open proximal end, a receiving space defined by the first and second side walls and the front wall, and a longitudinal axis extending between the distal end and the proximal end, wherein the proximal end is configured to receive at least one partial section of a receiving container in the receiving space;

forming a holding device for the sleeve directly in a region of the front wall on a side facing the receiving space, wherein the holding device comprises a plurality of holding elements formed or arranged on the front wall and distributed over the circumference, wherein each of the holding elements comprises a holding arm protruding from the front wall;

forming a retaining protuberance on the holding arm of each of the holding elements protruding in a direction towards the longitudinal axis;

forming a plurality of perforations through the front wall, wherein each of the perforations, seen in a projection section of each of the holding elements in an axial direction, is formed next to each of the holding elements in a radial direction towards the longitudinal axis and has a cross-section in the axial direction formed with a projection area equal to at least one projection area of the retaining protuberance;

arranging and connecting a needle device comprising a cannula directly with the front wall of the main body part or forming a needle device comprising a cannula on the front wall of the main body part as an integrated part such that a proximal cannula end of the cannula protrudes into the receiving space from the front wall;

moving the sleeve from the open proximal end towards the front wall of the holding device and supporting the open distal sleeve end in a circumferential direction between the perforations directly against the front wall in an axial direction;

placing the sleeve with the open distal sleeve end in a region of the holding elements formed on the front wall or arranged on the front wall to cover the cannula extending into the receiving space; and producing a contact area between each of the holding elements and the sleeve where the holding elements bear externally on the sleeve;

wherein each of the holding elements is displaceable on the front wall.

19. The method according to claim 18, wherein, as an additional part of the holding device on the front wall, a roughly cylindrical or frustum-shaped centering projection is formed as an integrated part of the front wall and extends into the open distal sleeve end of the sleeve.

20. The method according to claim 19, wherein each of the holding elements is arranged at a radial distance and forms a gap between each of the holding elements and the centering projection.

21. The method according to claim 19, wherein the perforation through the front wall is formed between the holding arm of each of the holding elements and the centering projection.

22. The method according to claim 18, wherein in a region of the open distal sleeve end, the sleeve is formed with a lip protruding beyond the sleeve in the radial direction.

23. The method according to claim 20, wherein the gap formed between each of the holding elements and the centering projection is of a distance larger than a wall thickness of the sleeve before the sleeve is placed over the centering projection and, after the sleeve is moved into the gap, each of the holding elements is shifted in the direction towards the longitudinal axis and brought to bear externally on the sleeve in the contact area.

* * * * *